(12) United States Patent
Hervé et al.

(10) Patent No.: US 7,296,693 B2
(45) Date of Patent: Nov. 20, 2007

(54) ANAEROBIC SLUDGE DIGESTER

(75) Inventors: Philip Hervé, Cournonsec (FR); Maunoir Siegfried, Montbazin (FR)

(73) Assignee: Ergalia, Paris (FR)

( * ) Notice: Subject to any disclaimer, the term of this patent is extended or adjusted under 35 U.S.C. 154(b) by 0 days.

(21) Appl. No.: 11/313,155

(22) Filed: Dec. 20, 2005

(65) Prior Publication Data

US 2006/0151390 A1    Jul. 13, 2006

Related U.S. Application Data

(63) Continuation of application No. PCT/FR04/01271, filed on May 21, 2004.

(51) Int. Cl.
*B01D 21/02* (2006.01)
(52) U.S. Cl. .................... 210/521; 210/532.1; 210/538
(58) Field of Classification Search ................ 210/521, 210/532.1, 538
See application file for complete search history.

(56) References Cited

U.S. PATENT DOCUMENTS 5,091,315 A    2/1992  McCarty et al. ......... 435/290.1
6,673,243 B2 *  1/2004  Srinivasan et al. ...... 210/532.2
2003/0034300 A1  2/2003  Srinivasan et al. ......... 210/610

FOREIGN PATENT DOCUMENTS

DE          3316720     11/1984
WO        WO01/79121   10/2001

OTHER PUBLICATIONS

EPO Search Report, Dec. 18, 2004.
Boopathy, R. et al.; "Anaerobic Digestion of High Strength Molasses Wastewater Using Hybrid Anaerobic Baffled Reactor"; Water Research, Elsevier Science Publishers, Amsterdam, NL, vol. 25, No. 7, pp. 785-790; XP000211206, ISSN: 0043-1354; p. 1, Figure 4, Jul. 1991.

* cited by examiner

*Primary Examiner*—Chester T. Barry
(74) *Attorney, Agent, or Firm*—Baker Botts L.L.P.

(57) ABSTRACT

A method is provided for introducing a fresh sludge flux whose concentration in terms of dry material is less than 40 g/l into the upstream part of digester, maintaining a thin sludge layer in the digester, circulating substantially horizontally effluents above and across the sludge layer and removing the effluents from the digester simultaneously with soluble products of sludge digestion. The cuvette of the digester is divided into sections by transverse walls, which are provided with communication openings in the lower part thereof.

8 Claims, 4 Drawing Sheets

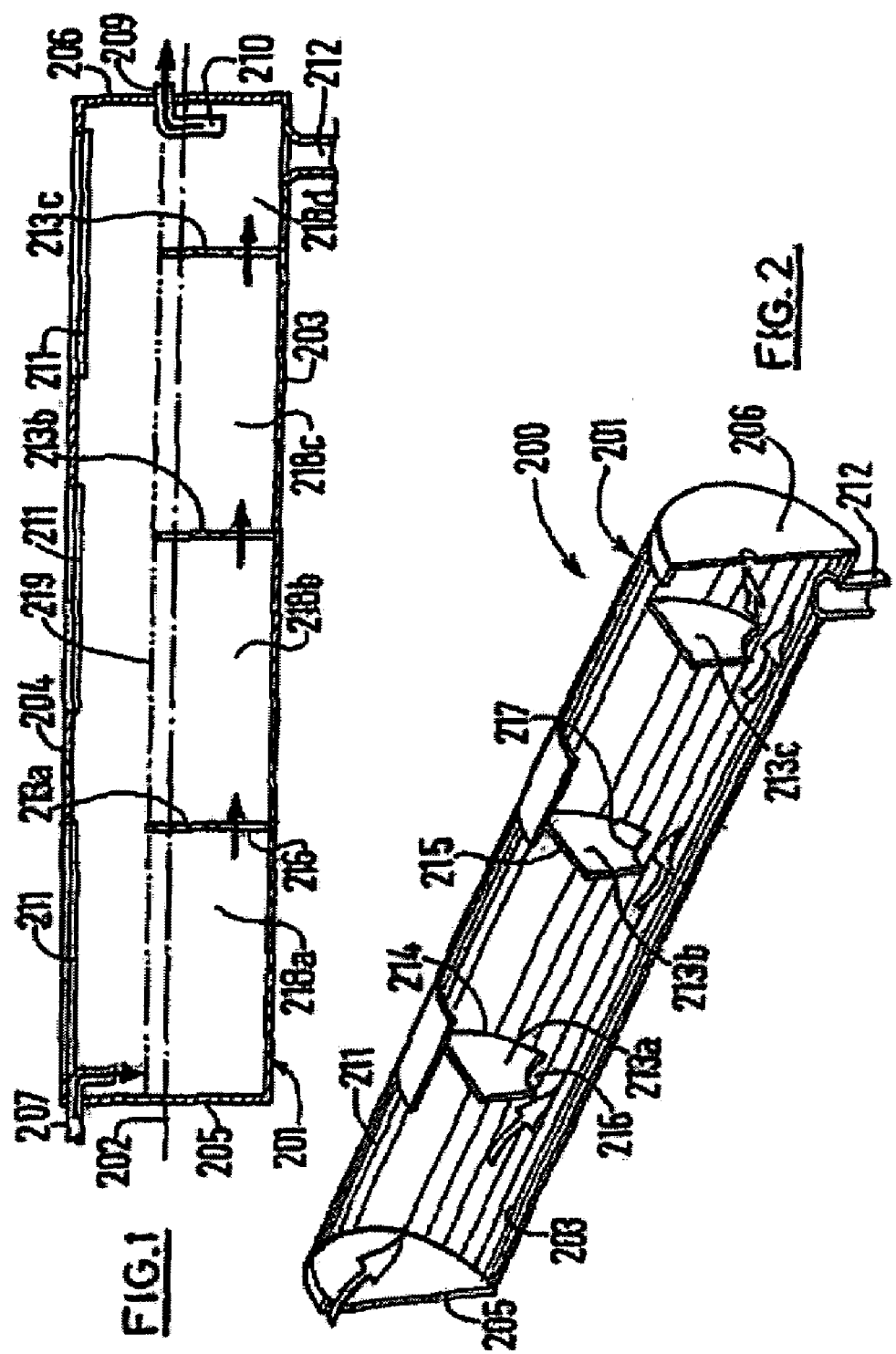

ANAEROBIC SLUDGE DIGESTER

CROSS-REFERENCE TO RELATED APPLICATIONS

This application is a continuation of copending International Application No. PCT/FR2004/001271 filed on May 21, 2004, which designates the United States and claims the benefit of French Application No. 0307631 filed Jun. 24, 2003.

BACKGROUND

The invention relates to a method for anaerobic digestion of sludge from the treatment of sewage effluents, an anaerobic digester of primary sludge containing effluents, as well as treatment plant comprising mainly such a digester.

Anaerobic digestion of sludge from the treatment of sewage effluents, for example household effluents, consists of hydrolysis and methane fermentation with considerable cell-destroying power, such as to be able to eliminate a considerable amount of the organic material contained in this sludge.

The sludge results, for example, from the settling of raw sewage. At the outlet of the digester, digested sludge is obtained on the one hand, together with effluents on the other, these two parts can then be separately subjected to a number of additional treatments.

Document U.S. Pat. No. 6,673,243 presents an anaerobic sludge digester comprising a tank divided into several successive compartments by means of transversal walls that do not reach the top of the tank. In the first upstream compartment, at the bottom, the sludge to be treated is inserted through a feeding pipe, the treated effluents being drained off from the final downstream compartment through a discharge pipe.

The median transversal wall comprises an opening at the bottom that allows the sludge and effluents to pass from the upstream compartment to the downstream compartment it defines.

On the other hand, none of the other transversal walls have a bottom opening. It follows that, on the one hand, the flow of the effluents alternates between rising and falling and, on the other hand, the sludge can build up in a compartment but cannot flow downstream after being digested. The effectiveness of the digester is therefore considerable diminished.

The invention aims to solve these problems.

SUMMARY

For this purpose, according to a first aspect, the invention relates to a method for anaerobic digestion of sludge, which comprises the following steps:
  inserting a flow of primary sludge in the upstream part of an anaerobic sludge digester, the said primary sludge containing effluents having a dry matter concentration of less than 40 g/l;
  maintaining a layer of sludge in the digester with a thickness of less than 0.6 m, the sludge being transformed by anaerobic digestion;
  making the said effluents circulate within the digester, above and through the layer of sludge, in a substantially horizontal manner at least in the useful part of the digester, from the upstream part towards the downstream part of the digester, and draining off the said effluents from the digester, so as to drain off the soluble products of sludge digestion from the digester;
  draining off the sludge from the digester.

Thus, from the start of the digestion by hydrolysis of the dry matter, the soluble components formed are extracted from the layer of sludge. In this way, the phenomena of inhibition or at least of slowing down of the digestion of the sludge in the tank are prevented or considerably reduced. The digestion therefore continues to take place at an optimized speed, and the necessary retention of the sludge in the digester is greatly reduced.

According to a possible embodiment of the invention, a layer of sludge with a thickness of less than 0.5 m is maintained in the digester. For example, the primary sludge has a dry matter concentration of less than 20 g/l.

According to a second aspect, the invention relates to an anaerobic digester of primary sludge containing effluents, with the aim implementing the method as described previously.

The digester comprises a tank with a substantially horizontal bottom, a pipe for feeding the primary sludge into the tank, a pipe for discharging the digested sludge from the tank, the said tank comprising at least one wall positioned transversally to the flow of the effluents, the wall defining an upstream and compartment and a downstream compartment, in order for the tank to have a first upstream compartment, into which the pipe for feeding primary sludge flows, and a final downstream compartment, from which the effluent discharge pipe flows.

According to the invention, the wall has, at the bottom, an opening to link the upstream compartment with the downstream compartment, so as to allow the passage of the sludge and the circulation of the effluents, above and through the layer of sludge maintained on the bottom of the tank, in a substantially horizontal manner from the first upstream compartment to the final downstream compartment.

The transversal wall extends from the bottom of the tank to a height that is less than the height of the tank, so as to allow the floating matter in the effluents to overflow from one compartment to another.

For example, the digester comprises at least two transversal walls, each of which has a linking opening at the bottom, such as to define at least three successive compartments in the tank.

Finally, according to a third aspect, the invention relates to a sewage effluent treatment plant comprising at least one such digester.

BRIEF DESCRIPTION OF THE DRAWINGS

Further characteristics of the invention can be seen from the following description of its embodiments, made in reference to the appended figures, in which:

FIG. 1 is a schematic section view, along a median longitudinal vertical plane, of a digester according to the invention;

FIG. 2 is a schematic perspective view of the digester of FIG. 1, seen along the same section;

DETAILED DESCRIPTION

Figure 3:
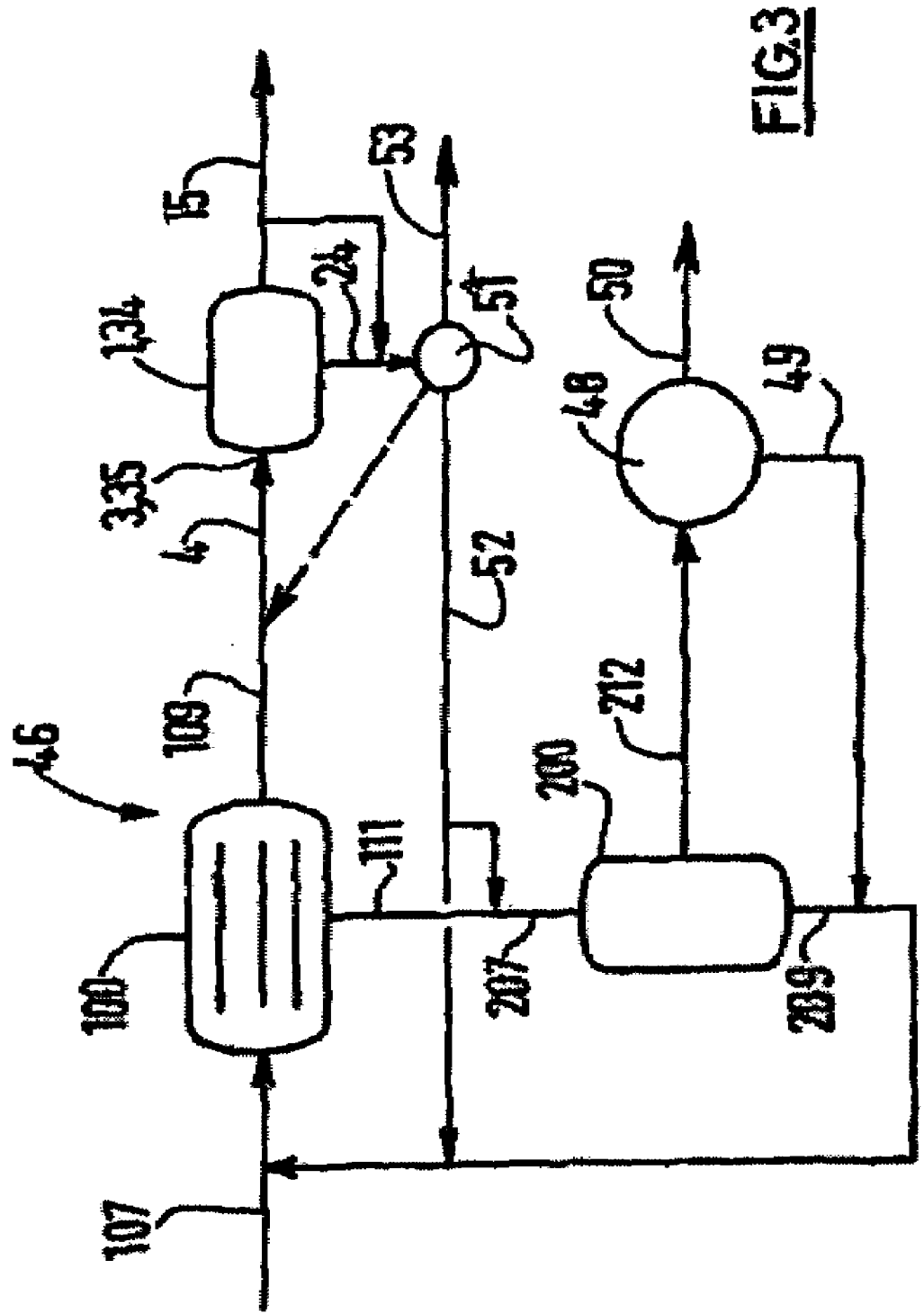
FIG. 3 is a schematic view of a treatment plant according to the invention, comprising mainly a settling tank, a filter or a filtering facility, and an anaerobic sludge digester, also showing the steps in a method for treating the sewage effluent in the said treatment plant.

Referring initially to FIGS. 1 and 2, a digester 200 according to the invention, intended for the treatment of primary sludge containing effluents is shown. This sludge is the result of a prior treatment of sewage effluents, for example, resulting from a settling process.

The digester 200 comprises a tank 201 with an axis 202, which is used here to define the term "longitudinal". The following description is made in relation to a tank 201 with a substantially cylindrical overall shape. However, the tank can also have a substantially rectangular vertical section: it is therefore possible to provide a very wide tank (on the horizontal plane), while keeping a reduced height.

The tank 201 is sealed, with the exception of three main openings and one or several inspection traps, as can be seen below, such as to guarantee the absence of oxygen in order to enable the methane fermentation. The tank 201 has a relatively low height (matching the diameter of the cylinder), of between 50 and 70 cm, and length comprised between 2 and 3 m. For example, the tank can have a volume of 250 to 300 l, for example, 270 l. In the case of a tank with a rectangular section, the volume increases according to its width, and can reach several thousand litres.

The tank 201 is positioned that the axis 202 is substantially horizontal. It comprises a substantially cylindrical side wall defining a bottom 203 and a top wall 204, as well as an upstream end wall 205 and a downstream end wall 206, which are substantially disc-shaped.

An opening is made at the top of the upstream wall 205 to allow the primary sludge to enter the digester 200 by means of a feeding pipe. The feeding pipe 207 extends inside the tank 201, substantially parallel to the axis 202 for a short length, and then vertically downwards for an approximate length of 10 cm, for example, such as to form inside the tank 201 and near the upstream wall 205, an elbow 208 that opens towards the bottom 203 of the tank 201. The opening of the feeding pipe 207 may be above or below the level of the effluents in the tank 201.

The downstream wall 206 has, substantially halfway up, an opening that allows the effluents to be drained off from the digester 200, by means of a discharge pipe 209.

The discharge pipe 209 extends inside the tank 201, substantially parallel to the axis 202 for a short length, and then vertically downwards for an approximate length of 10 cm, for example, such as to form, inside the tank 201 and near the downstream wall 206, an elbow 208 that opens towards the bottom 203 of the tank 201, forming a siphon-shaped inlet. The siphon-shaped inlet is located substantially halfway between the bottom 203 of the tank 201 and the level of the effluents maintained in the tank 201, so as not to allow the floating matter or the matter resting on the bottom 203 to escape.

The top wall 204 of the tank 201 can comprise at least one inspection trap 211; three inspection traps in the embodiment of the invention shown. Devices for sampling the gas produced by methane digestion can also be connected to the top wall 204.

Finally, an orifice for draining off digested sludge is made in the bottom 203 of the tank 201, near the downstream wall 206, the said orifice being connected to a discharge pipe 212 for the said sludge, with means for cutting off the said discharge pipe 212 being provided.

The digester 200 also comprises three transversal walls, respectively upstream 213a, intermediate 213b and downstream 213c. According to other foreseeable embodiments of the invention, the digester may comprise a different number of transversal walls, for example comprised between 1 and 6, as required in each case.

The walls 213a, b and c have substantially the same shape, namely that of a portion of a disc. The annular contour 214 of the walls matches the shape of the inside of the tank 201, from the bottom 203 to a height that is lower than the height of the tank, so that each wall 213a, b and c extends along the entire width of the tank 201. The walls 213a, b and c also have a top edge 215 that is substantially flat and horizontal, located at a distance from the bottom 203 of the tank 201 comprised between 40 and 70% of the height of the tank 201. For example, the height at the walls is somewhere between 20 and 40 cm, mainly 30 cm.

A linking opening 216, substantially disc-shaped, is made at the bottom of each wall 213a, b and c. The opening 216 comprises a substantially annular top edge 217 and extends from the bottom 203 of the tank 201 to a height comprised between 30 and 60% of the height of the transversal wall 213a, b and c. For example, the opening 216 extends to a height of approximately 10 to 15 cm.

Each transversal wall 213a, b and c defines an upstream compartment and a downstream compartment, so that the tank 201 of the digester 200 is divided longitudinally into four compartments 218a, 218b, 218c and 218d:

- a first upstream compartment the 218a, into which the primary sludge feeding pipe 207 flows, for example at the top;
- two consecutive intermediate compartments 218b, 218c;
- a final downstream compartment 218d, from which the effluent discharge pipe 209 flows.

The walls 213a, b and c make it possible to keep the sludge formed by agglomeration of the suspended matter in each compartment 218a to 218d, while the excess floating matter is able to pass by overflowing, from an upstream, compartment to a downstream compartment, or vice-versa.

The axial lengths of the compartments can be similar or, as an alternative, different. In the example shown, the first three compartments 218a, b and c have substantially identical lengths, while the final downstream compartment 218 is shorter, approximately half the length of the other compartments.

The number of compartments and the length of the digester can be reduced or, on the contrary, increased to refine the treatment.

The following is a description of the operation of the digester 200.

The primary sludge containing effluents is inserted in the tank 201 of the digester 200 by means of the feeding pipe.

"Primary sludge" is used here to refer to sludge that has a relatively low concentration of dry matter, lower than 25 g/l, or even lower than 20 g/l. It is possible particularly to insert sludge with a concentration comprised between 5 and 10 g/l into the digester. A lower concentration is possible, but the process becomes less cost-effective (larger digester volume, larger pumping flows, etc.).

This sludge can be the result of a settling process, and thus still obviously contain effluents. As an alternative, it can be previously concentrated sludge (dry matter concentration of 10 to 15%), mainly in order to facilitate transporting it from one treatment site to another.

In this case, the concentrated sludge is diluted with diluting effluents—for example, settled effluents that result from settling sewage effluents—before being inserted in the digester, so as to obtain a dry matter concentration that is compatible with the process.

The sludge settles on the bottom 203 of the tank 201 in the form of a thin stable layer, for example, less than 0.5 m, or even less than 0.3 m. According to a specific embodiment, the thickness of the layer of sludge can be less than 0.2 m. A level 219 of effluents is maintained in the tank 201, as shown in FIGS. 1 and 2. The level 219 of effluents is substantially at the same height as the top end of the same as discharge pipe 209 and the top edge 215 of the walls 213a, b and c.

The sludge is gradually broken down inside the digester 200. As it is digested, the sludge liquefies and passes into the consecutive compartments 218a to 218d, through the linking openings 216 made in the transversal walls 213a to c.

As regards the effluents, they flow substantially parallel to the axis 202, at least in the useful part of the tank 201, in other words, excluding the feeding and draining areas, where the effluents respectively flow in a locally downward direction from the feeding pipe 207 towards the bottom 203 of the tank and in an upward direction from the bottom 203 of the tank towards the discharge pipe 209.

The effluents therefore circulate substantially horizontally through the openings 216 between the bottom 203 of the tank 201 and the top edge 217 of the said openings 216, and do so from the first upstream compartment 218a towards the final downstream compartment 218d. During this flow, the effluents circulate above and through the layer of sludge. In this way, on the one hand, they carry with them the soluble products that result from the digestion of the sludge and, on the other hand, they force the sludge to move towards the compartments that are further downstream.

The effluents and the soluble products are then drained off from the tank 201 through the discharge pipe 209 and transported, as required, to another treatment unit.

The digested sludge contained in the final downstream compartment 218d is drained off through the discharge pipe 212, through the simple action of gravity or with the help of a suitable pumping device. The emptying processes can be either partial or complete, and either regular (periodic emptying of the digester, or consisting of periodic or continuous emptying, daily for example. As an alternative, the tank 201 is unequipped with the sludge discharge pipe, the sludge therefore being temporarily stored in the digester 200 and periodically drained off via the traps 211.

The digester according to the invention makes it possible to eliminate by liquefaction or gasification at least 40% of the dry matter in the sludge and up to over 90%, and to do so with a retention of the sludge in the digester comprised between 5 and 15 days, without needing to heat the digester, as long as its temperature remains above 10.C. Shorter retention is possible if the digester is heated (for example to a temperature comprised between 20 and 35° C.) since the performance of the digester is improved.

In these conditions, the concentration of the digested sludge is greatly facilitated, since only 50% to under 10% of sludge remains.

This can be compared with the methods of the previous technique, in which the sludge is concentrated prior to entering the digester. Its retention, in the form of a relatively thick layer is generally comprised between 12 and 40 days, the digester must be heated to between 25 and 35° C., and all this to obtain elimination of around 30% of the dry matter in the sludge.

Next is a description of a sewage effluent treatment plant 46, made in reference to FIG. 3.

The raw sewage is passed through a feeding pipe 107 into a primary settling tank 100, such as to be rid of a considerable part of its suspended matter.

The primary settling tank 100 comprises a discharge pipe 109 for the settled effluents connected, at the inlet of the effluents, to a filter 1 or a filtering facility 34 comprising several filters 1 operating in parallel, by means of a feeding pipe 4, and means for draining off the sludge that results from settling.

The sludge that results from the primary settling is drained off towards the digester via draining means, such as a discharge pipe 111, connected to the pipe 207 that feeds primary sludge into the digester 200.

The effluent discharge pipe 209 is connected to the feeding inlet of effluents to be settled in the primary settling tank 100. The evacuation outlet of the digested sludge is connected, via the discharge pipe 212 to the inlet of a sludge concentrator 48.

The sludge concentrator 48 comprises a wastewater outlet 49 connected to the feeding inlet of effluents to be settled in the primary settling tank 100, possibly via the pipe 209 for discharging the effluents from the digester 200.

The sludge concentrator 48 also comprises a concentrated sludge outlet 50. This sludge can be suitably conditioned and treated subsequently with a view to being used for the purpose of enriching soil. It can also be sent to a dump or to an incineration unit.

The effluents filtered by the filter 1, or the filtering facility 34, are drained off through a discharge pipe 15. If the filter 1 is able to retain the suspended matter contained in the effluents to be filtered, the filtered effluents are directly rejected. In the opposite case, the filtered effluents are directed towards the inlet of a secondary settling tank 51.

The filter 1 also comprises drawing-off outlets that allow the biomass to be drained off through drawing-off pipes 24, which may be connected either to the inlet to the secondary settling tank 51 or, when the plant is not equipped with a secondary settling tank, to the feeding inlet of effluents to be settled in the primary settling tank 100 or to the feeding inlet of primary sludge to the digester 200.

The secondary settling tank 51 comprises means for draining off the sludge that results from settling, connected either to the feeding inlet of effluent to be settled in the primary settling tank 100, via a discharge pipe 52, which may flow into the pipe 209, or to the feeding inlet of primary sludge to the digester 200. A part of this sludge can also be sent back to the top of the filter 1 so as to maintain the biomass at a desired level.

In addition, the secondary settling tank 51 comprises a discharge pipe 53 for the settled effluent.

Figure 4:
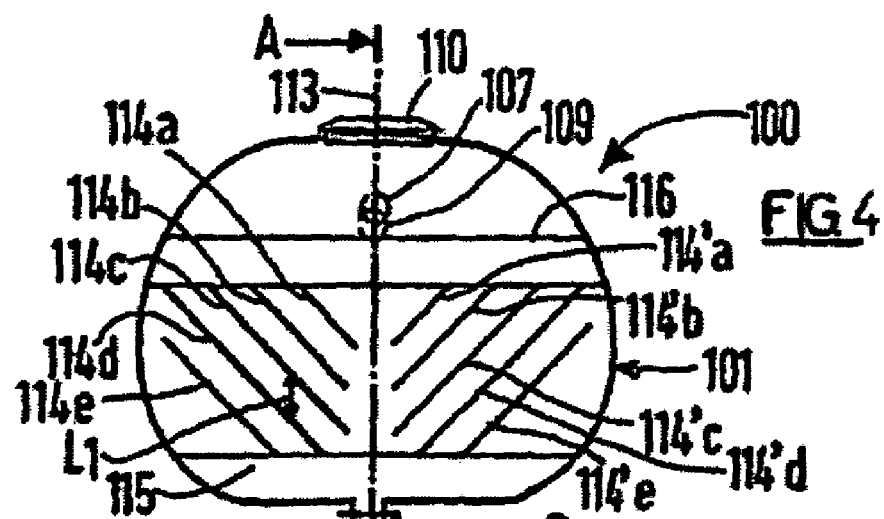
FIG. 4 is a schematic cross-section view of a settling tank in the treatment plant, according to a possible embodiment of the invention.
Figure 5:
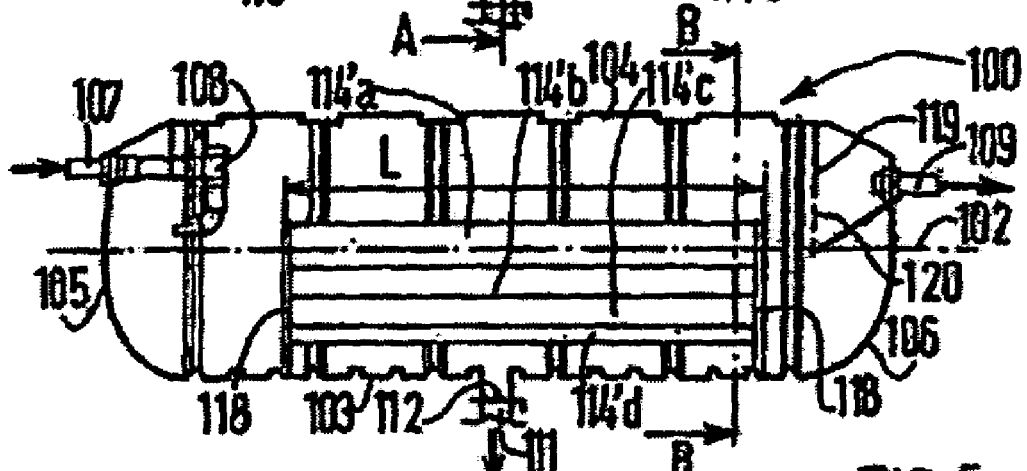
FIG. 5 is a section view, along the line AA, of the FIG. 6 settling tank in FIG. 4.
Figure 6:
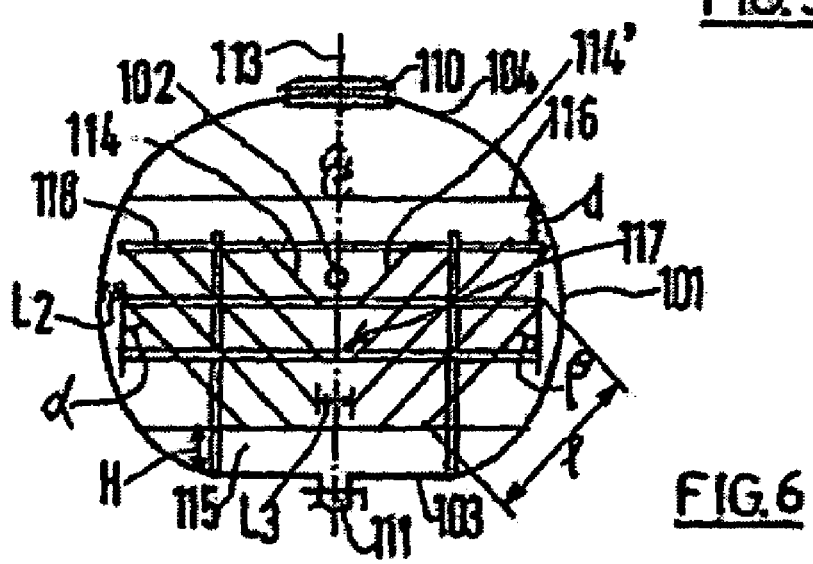
FIG. 6 is a section view of the settling tank in FIG. 4, along the line BB of FIG. 5.

In a possible embodiment of the invention, shown in FIGS. 4 to 6, the primary settling tank 100 and/or the secondary setting tank 51 comprise, according to a general definition:
  a tank 101 with a bottom 103 and which has, in relation to the direction of flow of the effluents, an upstream part into which a sewage effluent feeding pipe 107 flows and a downstream part from which the settled effluent discharge pipe 109 flows.
  a settling surface arranged in the tank 101, formed by the top face of at least one settling panel 114, 114', the said panel having a medium plane that is substantially parallel to the direction of flow of the effluents and tilted, according to a plane that is a transverse to the flow of the effluents, and in relation to the orthogonal projection of the vertical of the said transverse plane, at an angle.

A first assembly of at least one settling panel 114 is tilted at a first angle α of between approximately 15° and 60°, and at least one second assembly of at least one settling panel 114' is tilted at a second angle β of between approximately 15° and 60°, the angles α, β, the surface finish and the friction coefficient of the panels being chosen so that, when the effluents flow into the tank, the sludge settles on the settling surface and then slides towards the bottom of the tank, at least one draining passage 117 for the sludge being provided between the panels of the two assemblies, so as to allow the sludge collected on the top faces of the panels to fall through the action of gravity towards the bottom 103 of the tank 101.

The tank 101 is substantially cylindrical, buried so that the axis 102 is horizontal, and. sealed with the exception of four openings:

an opening for the inlet of effluents to be settled, made in the upstream end wall 105, the feeding pipe 107 extending into the tank by means of an elbow 108 that is open towards the upstream direction;

an opening for discharging the settled effluents, made in the downstream end wall 106, a siphon-shaped wall 119 equipped with an opening 120 being provided so as to keep the floating matter inside the tank;

an inspection trap 110 in the top wall 104;

possibly, an orifice for discharging the sludge that results from settling, connected to a discharge pipe 111, cut-off means 112 also being provided. As an alternative, the evacuation means can comprise force pumps submerged in the tank 101 or suction pipes that rise back up to the top of the tank 101 and are connected to a suction pump.

The tank comprises assemblies of two panels, arranged symmetrically in relation the vertical, longitudinal, median plane 113 of the tank.

The first such assembly (on the left) comprises five panels 114a to 114e that are substantially parallel, vertically stacked and separated from each other by a substantially constant distance L1 of approximately 30 cm. The panels 114a to 114e are tilted from top to bottom from the substantially vertical side wall of the tank towards the vertical plane 113, at an angle of approximately 4520 .

The panels 114 have different widths 1 depending on their distance from the bottom 103 of the tank, but lengths L (parallel to the flow of the effluents) that are substantially identical. The panels 114 are separated from the vertical side wall of the tank 101 by a horizontal distance L2 of approximately 10 cm, for the suspended matter to pass in between them, and from the bottom 103 by a vertical height H of almost 30 cm, so as to create a space 115 for the accumulation of the sludge that results from settling. Finally, the top end of the panels is located at a distance d above the level 116 of the effluents inside the tank.

The second assembly (on the right) is symmetrical to the first in relation to the vertical plane 113, and comprises five panels 114'a to 114'e. The horizontal separation L3 between the first and second panel assemblies is around 30 cm, so as to create a space 117 that allows the sludge collected in the panels to fall towards the bottom, being directed and collected in the central area of the bottom 103 of the tank 101.

Support and attachment means 118 of the panels 114, 114' to the tank 101 are placed in the proximity of the upstream and downstream ends of the said panels.

According to a possible embodiment of the invention, the settling tank 100 comprises, in relation to the flowing direction of the effluents, at least a first and second series of panels 114, 114', the second series being located downstream from the first series, the said series each comprising at least a first and second assembly made up of at least one panel, so as to further improve the extraction of the sludge.

Figure 7:
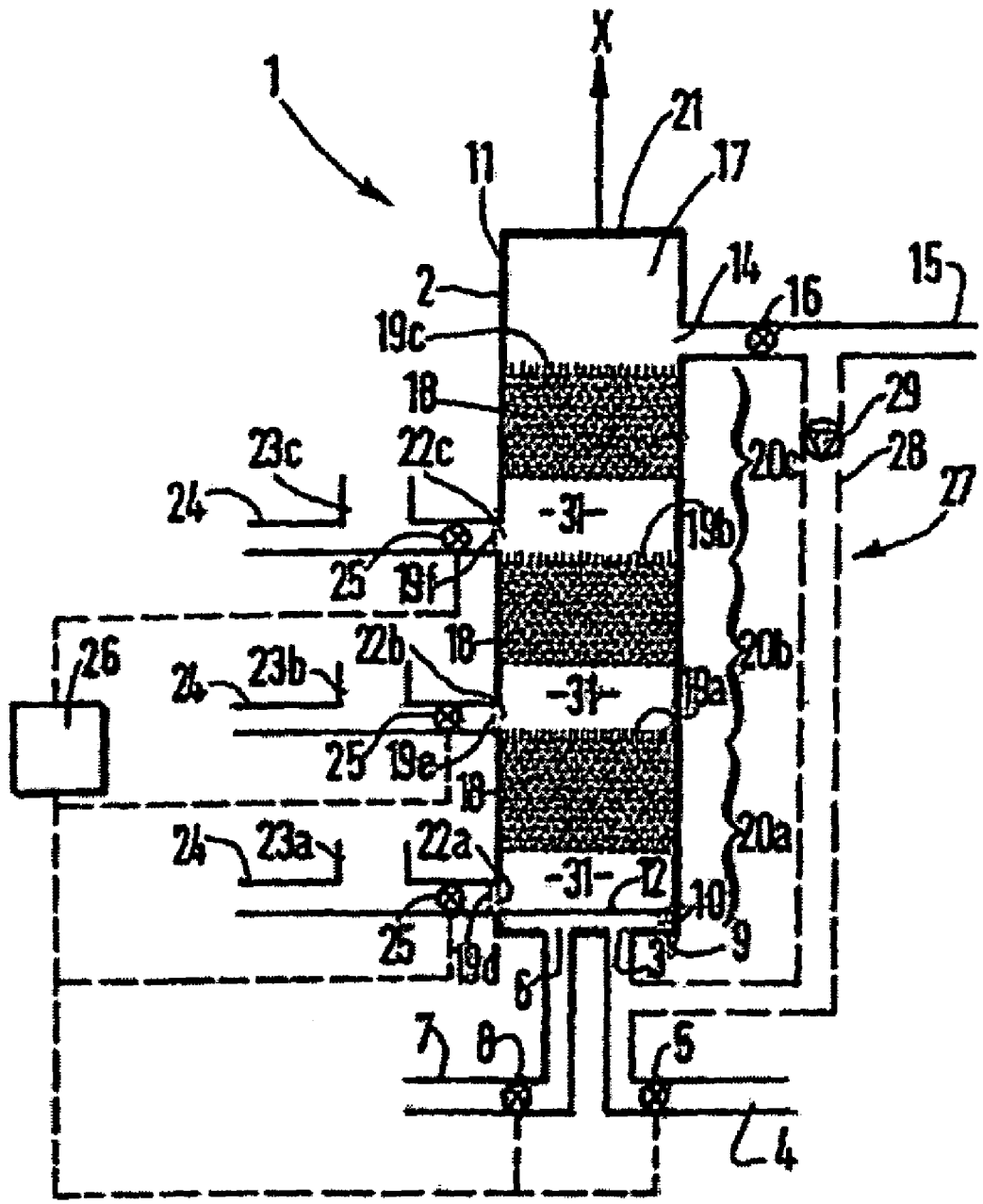
FIG. 7 is a schematic longitudinal vertical section view of a filter in the treatment plant, according to a possible embodiment of the invention.

In a possible embodiment of the invention, shown in FIG. 7, the filter 1 comprises, according to a general definition, a reaction chamber 2 in which the flow of effluents to be filtered is arranged so as to flow from the bottom up, the said reaction chamber 2 comprising:

at the bottom, an inlet 3 for effluents to be filtered and an inlet 6 for oxygenated gas;

and, at the top, an outlet 14 for the filtered effluents;

filtering means 18 comprising layers of particles of a solid material forming supports and a biomass stuck to the surface of the said supports, the said filtering means 18 having a density that is lower than the density of the effluents to be filtered and being placed between the inlet 3 of the effluents to be filtered and the outlet 14 of the filtered effluents.

The reaction chamber 2 is subdivided into at least three stacked compartments forming levels in between at least two walls 19a, 19b, 19c provided with openings, the said openings being disposed such as to retain the filtering means 18, so as to create the following inside the reaction chamber:

at least two filtering levels 20a, 20b, 20c;

and a top outlet level 17, the outlet 14 of the filtered effluents flowing from the top outlet level 17.

Each filtering level 20a, 20b, 20c is provided with a layer of its own filtering means 18 and comprises, at the bottom, an outlet 22a, 22b, 22c for drawing off the excess biomass, the amount and the density of the filtering means in each filtering level 20a, 20b, 20c being such that, in drawing-off mode, the bottom part of at least the bottom level or levels 20a, 20b from which the drawing-off outlet 22a, 22b flows, is unequipped with filtering means, so as to enable the recovery of the excess biomass.

The reaction chamber 2 defines a main axis X with a vertical orientation. The inlet 3 of the effluents to be filtered is connected to a feeding pipe 4 provided with a gate 5, and the oxygenated gas inlet 6 is connected to a feeding pipe 7 provided with a gate 8. According to an embodiment of the invention, the two inlets 3, 6 are made in the bottom wall 9 of the reaction chamber 2 and flow into an inlet compartment 10 delimited by a part of the side wall 11 of the reaction chamber and by a top inner wall 12 that is permeable to the effluents and to the oxygenated gas.

The outlet 14 of the filtered effluents is connected to a discharge pipe 15 provided with a gate 16, and flows from a top outlet level 17 of the reaction chamber.

The reaction chamber 2 is subdivided into stacked compartments forming filtering levels by means of grilles 19a, 19b, 19c, the top outlet level 17, formed between the top wall 21 of the reaction chamber and the top wall 19c placed opposite, being unequipped with filtering means.

Each filtering level 20a, 20b, 20c comprises at the bottom an outlet 22a, 22b, 22c for drawing off the excess biomass, connected to a drawing-off pipe 24 equipped with a gate 25. A compartment 23a, 23b, 23c may be provided for recovering the said excess biomass.

The filtering means 18 are designed to float, at least in certain compartments, in drawing-off mode, such as to form a free bottom space 31 unequipped with filtering means. The grilles 19a, 19b, 19c make it possible to retain the filtering means 18. A device 26 for detecting the amount of excess biomass can also be provided.

The filter 1 can comprise means 27 for returning the filtered effluents, comprising a pipe 28 connected to a pump 29, for additional treatment of at least part of the filtered effluents.

During the filtering phase, the effluents and the gas circulate in an upward direction through the various filtering levels. The filtered effluents are drained off through the pipe 15 and the biomass remains on the supports. The feeding of effluents and/or gas can be continuous or intermittent.

During the washing phase, the excess biomass of the chosen level is recovered via the relevant drawing-off pipe 24 by means of a downward flow of the effluents contained in the reaction chamber 2.

The invention claimed is:

1. An anaerobic sludge digester, comprising:
   a tank having a substantially horizontal bottom;
   a first pipe connected to the tank at an upstream wall that feeds the tank with primary sludge;
   a second pipe connected to the tank at a downstream wall that draws off effluents from the tank; and
   at least two compartments, wherein the compartments are separated by at least one transverse wall having an opening at an end proximate to the bottom of the tank, and disposed within the tank transverse to the flow of effluents,
   wherein the at least one transverse wall allows the passage of sludge and the circulation of effluents, above and through the layer of sludge maintained on the bottom of the tank, in a substantially horizontal direction throughout substantially the entirety of the upstream and downstream compartments.

2. The digester according to claim 1, wherein the at least one transverse wall extends from the bottom of the tank to a height below the top of the tank, so as to allow the overflowing of the floating matter in the effluents from one compartment to another.

3. The digester according to claim 2, wherein the at least one transverse wall extends from the bottom of the tank to a height of between approximately 40 and 70% of the height of the tank.

4. The digester according to claim 1, wherein the opening in the at least one transverse wall extends from the bottom of the tank to a height of between approximately 30 and 60% of the height of the wall.

5. The digester according to claim 1, wherein the opening in the at least one transverse wall has a substantially annular top edge.

6. The digester according to claim 1, wherein the tank is substantially cylindrical in shape and has a substantially horizontal axis.

7. The digester according to claim 1, wherein the second pipe comprises a siphon-shaped inlet disposed substantially halfway between the bottom of the tank and the level of the effluents inside the tank.

8. The digester according to claim 1, further comprising an evacuation orifice formed in the bottom of the tank and a pipe connected to the evacuation orifice for discharging the sludge.

* * * * *